(12) United States Patent
Devens, Jr. et al.

(10) Patent No.: US 9,180,620 B2
(45) Date of Patent: Nov. 10, 2015

(54) MEDICAL BALLOONS

(75) Inventors: Douglas A. Devens, Jr., St. Paul, MN (US); Daniel James Horn, Shoreview, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2698 days.

(21) Appl. No.: 10/645,055

(22) Filed: Aug. 21, 2003

(65) Prior Publication Data

US 2005/0043679 A1 Feb. 24, 2005

(51) Int. Cl.

| | |
|---|---|
| *A61M 25/10* | (2013.01) |
| *B29C 49/22* | (2006.01) |
| *B29C 47/00* | (2006.01) |
| *B29C 47/26* | (2006.01) |
| *B29C 47/28* | (2006.01) |
| *B29C 47/06* | (2006.01) |
| *B29C 49/04* | (2006.01) |
| *B29K 21/00* | (2006.01) |
| *B29K 23/00* | (2006.01) |
| *B29K 27/06* | (2006.01) |
| *B29K 55/02* | (2006.01) |
| *B29K 67/00* | (2006.01) |
| *B29K 71/00* | (2006.01) |

(Continued)

(52) U.S. Cl.
CPC ............ *B29C 49/22* (2013.01); *A61M 25/1002* (2013.01); *A61M 25/1029* (2013.01); *B29C 47/0023* (2013.01); *B29C 47/065* (2013.01); *B29C 47/26* (2013.01); *B29C 47/28* (2013.01); *A61M 25/104* (2013.01); *A61M 2025/1079* (2013.01); *B29C 47/0026* (2013.01); *B29C 47/06* (2013.01); *B29C 49/04* (2013.01); *B29C 2049/228* (2013.01); *B29K 2021/00* (2013.01); *B29K 2023/083* (2013.01); *B29K 2027/06* (2013.01); *B29K 2055/02* (2013.01); *B29K 2067/00* (2013.01); *B29K 2067/006* (2013.01); *B29K 2071/00* (2013.01); *B29K 2075/00* (2013.01); *B29L 2031/7542* (2013.01)

(58) Field of Classification Search
CPC ............ A61M 25/10; A61M 25/1002; A61M 25/104; A61M 25/1029; A61M 2025/1075; A61M 2025/1059
USPC ........................................ 604/103.06–103.08
See application file for complete search history.

(56) References Cited

U.S. PATENT DOCUMENTS

| | | |
|---|---|---|
| 3,752,617 A | 8/1973 | Burlis et al. |
| 4,963,313 A | 10/1990 | Noddin et al. |
| 5,195,969 A | 3/1993 | Wang et al. |

(Continued)

FOREIGN PATENT DOCUMENTS

| | | |
|---|---|---|
| DE | 20 2004 007 930 U1 | 9/2004 |
| WO | WO 01/32398 | 5/2001 |

OTHER PUBLICATIONS

International Search Report for PCT/US2004/025716, mailed Jan. 13, 2005/.

(Continued)

*Primary Examiner* — Victoria P Shumate
(74) *Attorney, Agent, or Firm* — Seager, Tufte & Wickhem LLP (57) ABSTRACT

Medical devices, such as medical balloons, and methods of making the devices, are disclosed. In some embodiments, the balloons include a portion, e.g., a layer, that varies in thickness.

16 Claims, 3 Drawing Sheets

(51) Int. Cl.
  *B29K 75/00* (2006.01)
  *B29L 31/00* (2006.01)

(56) References Cited

U.S. PATENT DOCUMENTS

| | | |
|---|---|---|
| 5,270,086 A | 12/1993 | Hamlin |
| 5,499,973 A | 3/1996 | Saab |
| 5,538,510 A | 7/1996 | Fontirroche et al. |
| 5,565,530 A | 10/1996 | Hattori et al. |
| 5,620,649 A | 4/1997 | Trotta |
| 5,714,110 A | 2/1998 | Wang et al. |
| 5,755,690 A * | 5/1998 | Saab .................. 604/103.06 |
| 5,759,172 A | 6/1998 | Weber et al. |
| 5,797,877 A | 8/1998 | Hamilton et al. |
| 5,797,878 A | 8/1998 | Bleam |
| 5,820,594 A | 10/1998 | Fontirroche et al. |
| 5,843,116 A * | 12/1998 | Crocker et al. ............. 606/192 |
| 5,915,969 A | 6/1999 | Linden |
| 5,961,765 A | 10/1999 | Kastenhofer |
| 6,004,339 A | 12/1999 | Wijay |
| 6,024,752 A | 2/2000 | Horn et al. |
| 6,120,364 A | 9/2000 | Laflamme |
| 6,124,007 A | 9/2000 | Wang et al. |
| 6,136,258 A | 10/2000 | Wang et al. |
| 6,328,925 B1 | 12/2001 | Wang et al. |
| 6,364,856 B1 * | 4/2002 | Ding et al. .............. 604/103.02 |
| 6,471,673 B1 | 10/2002 | Kastenhofer |
| 6,503,223 B1 | 1/2003 | Sekido et al. |
| 6,528,150 B2 | 3/2003 | Nazarova et al. |
| 6,540,721 B1 | 4/2003 | Voyles et al. |
| 6,579,484 B1 | 6/2003 | Tiernan et al. |
| 2001/0019762 A1 | 9/2001 | Nazarova et al. |
| 2002/0022824 A1 | 2/2002 | Kastenhofer |
| 2002/0045017 A1 | 4/2002 | Wang et al. |
| 2002/0081406 A1 | 6/2002 | Wang et al. |
| 2002/0098307 A1 | 7/2002 | Schwartz et al. |
| 2002/0122903 A1 * | 9/2002 | Ferrera et al. ............... 428/35.2 |
| 2002/0165523 A1 | 11/2002 | Chin et al. |
| 2003/0088265 A1 | 5/2003 | Kastenhofer |
| 2004/0267197 A1 * | 12/2004 | Blankenship ........... 604/103.06 |

OTHER PUBLICATIONS

U.S. Appl. No. 10/263,225, Bertolino et al.

* cited by examiner

MEDICAL BALLOONS

RELATED APPLICATION

This patent application is related to U.S. patent application entitled "Multilayer Medical Devices", Ser. No. 10/645,014, now U.S. Pat. No. 7,166,099, filed concurrently herewith and incorporated by reference in its entirety. A copy of Ser. No. 10/645,014 is attached as Appendix A.

TECHNICAL FIELD

The invention relates to medical balloons, and methods of making the same.

BACKGROUND

Medical balloons can be used to administer a variety of treatments. For example, in an angioplasty procedure, a balloon can be used to widen a constricted bodily vessel, such as a coronary artery. A balloon can also be used to deliver a tubular member, such as a stent, that is placed in the body to reinforce or to reopen a blocked vessel.

In angioplasty, the balloon can be used to treat a stenosis, or a narrowing of the bodily vessel, by collapsing the balloon and delivering it to a region of the vessel that has been narrowed to such a degree that blood flow is restricted. The balloon can be delivered to a target site by passing the catheter over an emplaced guidewire and advancing the catheter to the site. In some cases, the path to the site can be rather tortuous and/or narrow. Upon reaching the site, the balloon is then expanded, e.g., by injecting a fluid into the interior of the balloon. Expanding the balloon can expand the stenosis radially so that the vessel can permit an acceptable rate of blood flow. After use, the balloon is collapsed and withdrawn.

In stent delivery, the stent is compacted on the balloon and transported to a target site. Upon reaching the site, the balloon can be expanded to deform and to fix the stent at a predetermined position, e.g., in contact with the vessel wall. The balloon can then be collapsed and withdrawn.

Medical balloons can be manufactured by extruding a cylindrical tube of polymer and then pressurizing the tube while heating to expand the tube into the shape of a balloon. The balloon can be fastened around the exterior of a hollow catheter shaft to form a balloon catheter. The hollow interior of the balloon is in fluid communication with the hollow interior of the shaft. The shaft may be used to provide a fluid supply for inflating the balloon or a vacuum for deflating the balloon.

SUMMARY

The invention relates to medical balloons.

In one aspect, the invention features a medical device including a balloon having a first portion, and a second portion disposed on a selected portion of the first portion, wherein the first and second portions vary in thickness.

Embodiments may include one or more of the following features.

The first and second portions have different compositions and/or hardness. The first portion extends substantially the entire length of the balloon. The second portion is softer than the first portion. The second portion is disposed substantially entirely on the first portion. The portions extend substantially the entire length of the balloon. The portions vary continuously in thickness along the length of the balloon. One of the portions includes a step-wise change in thickness along the length of the balloon.

The balloon has a body portion, and the first portion is thicker at a first portion of the body portion than at another portion of the balloon. The balloon has a body portion, and the first portion is thicker at a first portion of the body portion than a cone portion of the balloon. The balloon has a body portion defined substantially entirely by the first portion. The balloon has a cone portion, and the thickness of the first portion is generally constant in the cone portion. The balloon has a cone portion, and the thickness of the first portion varies over a portion of the cone portion. The balloon has a cone portion, and the thickness of the second portion is generally constant in the cone portion. The balloon has a cone portion, and the thickness of the second portion varies over a portion of the cone portion. The balloon has a body portion and a cone portion that are more flexible than the body portion. The balloon has a proximal portion and a distal portion that is more flexible than the proximal portion.

In another aspect, the invention features a medical device including a balloon having a first portion, and a second portion disposed on a selected portion of the first layer, the second portion varying in thickness.

Embodiments may include one or more of the following features.

The second portion is softer than the first portion. The first and second portions have different hardness. The first portion extends substantially the entire length of the balloon. The second portion extends substantially the entire length of the balloon.

The balloon has a body portion and a cone portion, and the second portion is thinner on the body portion than on the cone portion. The balloon has a body portion substantially free of the second portion. The balloon has a body portion and a cone portion that is more flexible or less flexible than the body portion.

In another aspect, the invention features a medical device including a balloon having a body portion, a cone portion, and a first layer of polymer extending across a portion of the body portion and a portion of the cone portion, the first layer of polymer having a thickness in the body portion different than a thickness in the cone portion.

Embodiments may include one or more of the following features.

The thickness of the first layer in the portion of the cone portion is substantially constant. The thickness of the first layer in the portion of the cone portion tapers. The thickness of the first layer tapers increasingly from the cone portion to the body portion. The total thickness of the first and second layers is substantially constant in the body portion and in the cone portion. The first and second layers extend substantially the entire length of the balloon. The second layer is softer than the first layer. The first layer is thicker in the body portion than in the cone portion. The second layer is harder than the first layer. The body portion is less flexible than the cone portion. The body portion consists essentially of the first layer. The balloon further includes a second layer over a portion of the first layer, the second layer having a composition different than the first layer.

In another aspect, the invention features a method of making a medical device including forming a tube having a first layer and a second layer, the first layer varying in thickness, and forming the tube into a medical balloon. The tube can be extruded. Forming the tube into the medical balloon can include blow molding. The second layer can vary in thickness.

In another aspect, the invention features a medical balloon including a plurality of layers formed of a first material and a second material different than the first material, wherein at least one of the layers varies in thickness axially along the balloon. The balloon can include a body portion and a tapered portion, wherein the body and tapered portions having different stiffness. The balloon can include at least two layers.

Embodiments may have one or more of the following advantages. The balloon can have relatively flexible cone or waist portions. As a result, the flexibility of the balloon can be enhanced, which can allow the balloon to better navigate a tortuous path. The balloon can be formed efficiently, e.g., with high yields and/or low costs.

Other aspects, features, and advantages of the invention will be apparent from the description of the preferred embodiments thereof and from the claims.

DETAILED DESCRIPTION

Structure

Figure 1:
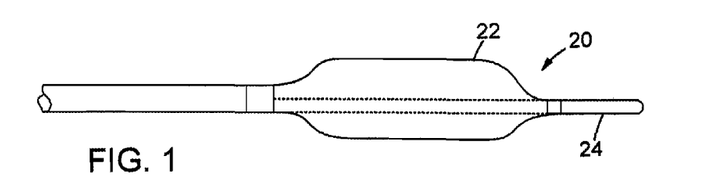
FIG. 1 is an illustration of an embodiment of a catheter carrying a balloon.
Figure 2:
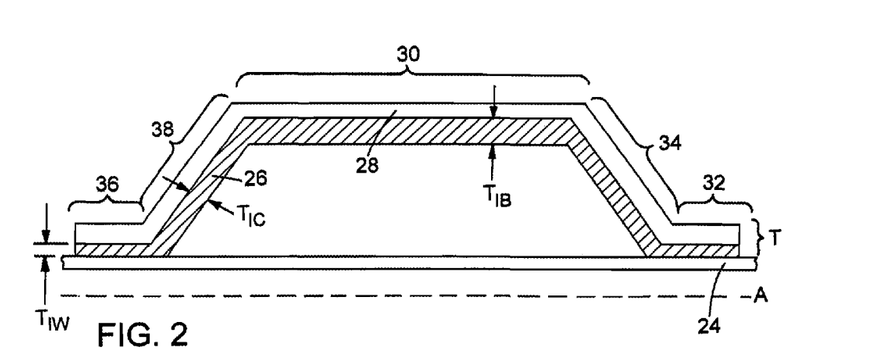
FIG. 2 is a cross-sectional illustration of an embodiment of a balloon.

Referring to FIG. 1, a balloon catheter 20 includes a balloon 22 carried by a catheter 24. Examples of balloon catheter are described, for example, in Wang, U.S. Pat. No. 5,915,969; Hamlin, U.S. Pat. No. 5,270,086; and exemplified by the MAVERICK® or SYMBIOT® catheter systems available from Boston Scientific Corp.-Scimed Life Systems, Inc. (Maple Grove, Minn.). As shown in FIG. 2, balloon 22 has a wall structure that includes multiple (as shown, two) polymer layers 26 and 28. Layers 26 and 28 are typically formed of different polymer compositions. The polymer compositions, the thickness or presence of the layers, and the overall thickness of the balloon wall (T) are selected to control characteristics of the balloon along its length (longitudinal or axial axis A) to enhance balloon performance. For example, the stiffness of the balloon can be varied along the axial length of the balloon to facilitate delivery of the balloon on a catheter into a tortuous body lumen such as a blood vessel. Portions of the balloon can be relatively flexible to enhance lateral flexibility and hence trackability, e.g., over a guidewire. In addition, inflation characteristics, bondability and stent-carrying characteristics of portions of the balloon can be controlled along the balloon to enhance the function of different portions of the balloon.

In FIG. 2, the wall thickness of the balloon is substantially constant and layers 26 and 28 extend substantially along the length of the balloon. The thickness of the layers is different in different portions of the balloon. Balloon 22 includes a body portion 30, a distal waist 32, a distal cone 34, a proximal waist 36, and a proximal cone 38. Body portion 30 has the largest diameter when the balloon is expanded, for example, to engage tissue under treatment, to expand a body lumen, or to deliver a stent. Waists 32 and 36 are portions of balloon 22 that are attached to catheter 24. Cones 34 and 38 generally extend from body portion 30 to waists 32 and 36, respectively. The thickness of the inner layer in the body portion $T_{IB}$ is greater than the thickness of the inner layer in the cone portions $T_{IC}$ or waist portions $T_{IW}$. In embodiments, the inner layer is a relatively stiff, inelastic, high burst strength polymer composition, and the outer layer is a less stiff, more flexible and compliant, and lower durometer polymer. Since the inner layer is relatively thick in the body portions, the properties of high strength and inelasticity are enhanced in this portion, which can improve performance characteristics such as inflation to defined diameters and predictable burst pressures. The presence of the outer layer in the body portion improves pinhole resistance and stent delivery characteristics. For example, a stent can become nested or embedded slightly into the outer layer. Since the inner layer is relatively thin in the waist and cone portions, flexibility is enhanced which improves performance characteristics such as trackability.

In some embodiments, within body portion 30, layer 28 makes up from about one percent to about 95% of the total balloon wall thickness and layer 26 makes up the balance. For example, within body portion 30, layer 28 can make up greater than or equal to about 1%, 5%, 10%, 15%, 20%, 25%, 30%, 35%, 40%, 50%, 60%, 70%, 80%, or 90% of the total balloon wall thickness; and/or less than or equal to about 95%, 90%, 80%, 70%, 60%, 50%, 45%, 40%, 35%, 30%, 25%, 20%, 15%, 10%, or 5% of the total balloon wall thickness. In certain relatively flexible portions, e.g., cone portions 34 and 38 or waists 32 and 36, layer 26 make up from about one percent to about 95% of the total balloon wall thickness and flexible polymer makes up the balance. For example, within cone portions 34 and/or 38, and/or waists 32 and 36, layer 26 can make up greater than or equal to about 1%, 5%, 10%, 15%, 20%, 25%, 30%, 35%, 40%, 50%, 60%, 70%, 80%, or 90% of the total balloon wall thickness; and/or less than or equal to about 95%, 90%, 80%, 70%, 60%, 50%, 45%, 40%, 35%, 30%, 25%, 20%, 15%, 10%, or 5% of the total balloon wall thickness. For example, inner layer 26 can be formed of a relatively stiff material such as a biaxially oriented, relatively crystalline polymer composition. Suitable polymer include PET or PEBAX® 7233 (72 Shore D). Outer layer 28 can be formed of a relatively flexible, more amorphous polymer. Suitable polymers include PE or PEBAX® 7033 (69 Shore D). The particular thickness of the layers can depend, e.g., on the materials used and/or the desired flexibility. In other embodiments, layer 26 can include one or more materials that are softer than one or more materials in layer 28.

In embodiments in which the balloon wall thickness (T) is not constant, thickness variations can be used to contribute variations in properties along the balloon. For example, if body portion 30 includes relatively more stiff material than cones 34 and 38 and/or waists 32 and 36, the body portion can be more flexible than the cones and/or waists, for example, if the body portion is substantially thinner, e.g., due to blow molding (described below).

Figure 3:
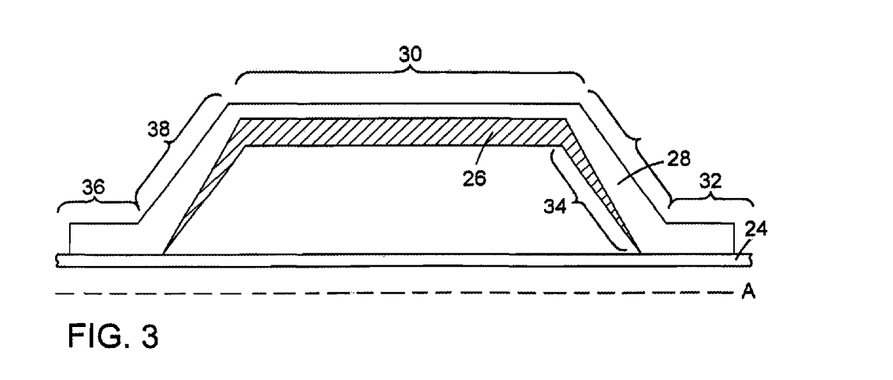
FIG. 3 is a cross-sectional illustration of an embodiment of a balloon.
Figure 4:
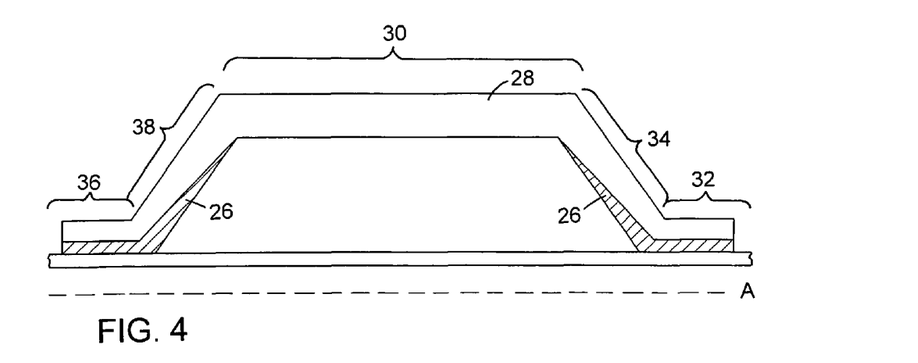
FIG. 4 is a cross-sectional illustration of an embodiment of a balloon.
Figure 5:
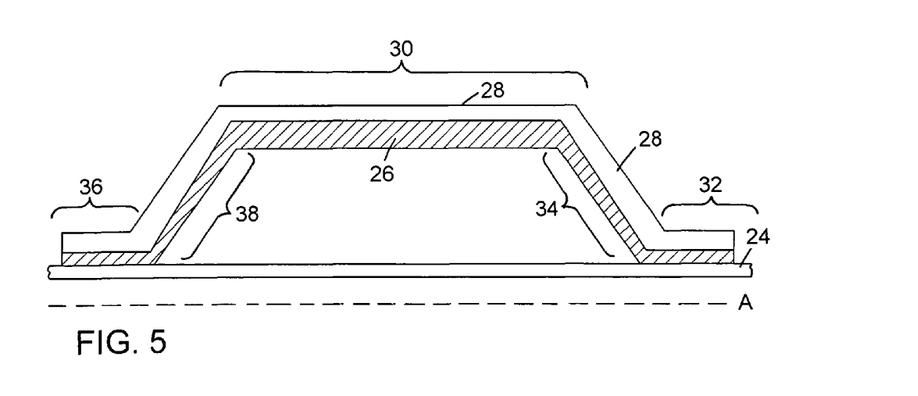
FIG. 5 is a cross-sectional illustration of an embodiment of a balloon.

FIG. 3 shows another embodiment of a portion of a balloon in which stiff inner layer 26 defines all of body portion 30, which does not include any soft material. The stiff body portion can provide predictable expansion and burst pressures. As shown, inner layer 26 tapers in thickness from waists 32 and 36 to body portion 30, but in some embodiments, the inner layer in the waists and/or cones can have the same thickness profile as shown in FIG. 2. In other embodiments, inner layer tapers decreasingly in thickness from waists 32 and 36 to body portion 30 (FIG. 4). As shown in FIG. 4, layer 26 can be softer and less stiff than layer 28. FIG. 5 shows another embodiment in which inner layer 26 tapers increasingly in thickness from waists 32 and 36 to body portion 30, which includes both the inner layer and outer layer 28. Outer layer 28 can provide good stent securement and pinhole resistance.

Figure 6:
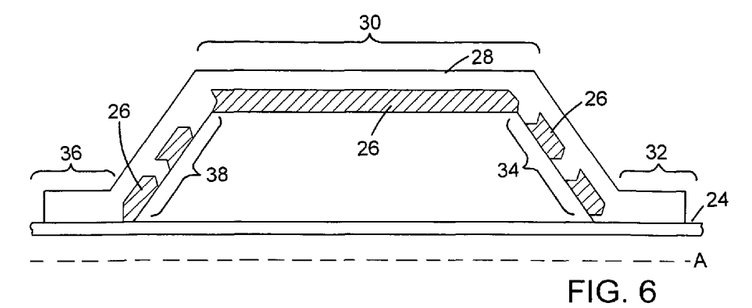
FIG. 6 is a cross-sectional illustration of an embodiment of a balloon.

One or more of the layers can extend continuously or discontinuously along the length of balloon 22. FIG. 6 shows an example of inner layer 28 that extends discontinuously, e.g., portions of the inner layer are separated by another material, as shown, outer layer 26. The discontinuous inner layer 28 in cones 34 and 38 can taper in thickness (e.g., FIGS. 3 and 4) or be relatively constant in thickness (e.g., FIG. 2). Inner layer 28 can define all of body portion 30 or a portion thereof (e.g., FIG. 2). Examples of layers that extend continuously are shown in FIGS. 2 and 3.

Figure 7:
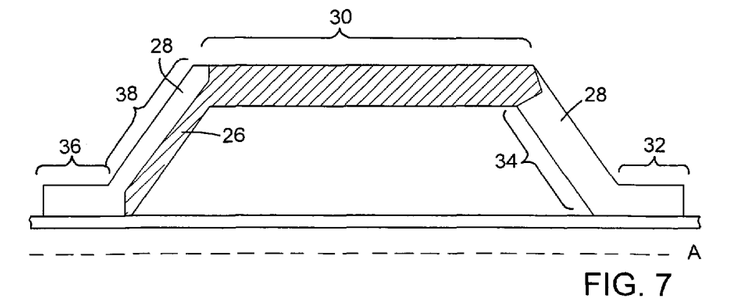
FIG. 7 is a cross-sectional illustration of an embodiment of a balloon.

The thickness of one or more layers can be asymmetrical about a central, radial cross section of balloon 22. Referring to FIG. 7, inner layer 26 is relatively thin in proximal cone 38 and is relatively thick in body portion 30. Distal of body portion 30, inner layer 26 terminates such that distal cone 34 is substantially defined by soft outer layer 28. As a result, the distal portion (cone 34 and waist 32) of balloon 22 can be highly flexible, which can improve the trackability of the balloon. The relatively stiffer proximal portion can improve burst pressures.

The layers can be asymmetrically distributed in the radial direction of the tube. For example, for a balloon having multiple layers of the same composition (e.g., FIG. 8 below), the layers can be arranged closer to an outer surface of the balloon than to an inner surface of the balloon. In other embodiments, the layers can be evenly distributed in the radial direction of the tube.

In certain embodiments, one or more layers can have along their axial lengths a minimum thickness of at least about 0.02 micron (e.g., at least about 0.05 micron, at least about 0.1 micron, at least about 0.25 micron, at least about 0.5 micron, at least about 0.75 micron, at least about one micron, at least about 1.5 microns, at least about 2 microns, at least about 2.5 microns, at least about 3 microns, at least about 3.5 microns), and/or a maximum thickness of at most about 20 microns (e.g., at most about 15 microns, at most about 10 microns, at most about nine microns, at most about eight microns, at most about seven microns, at most about six microns, at most about five microns, at most about four microns, at most about three microns, at most about two microns, at most about one micron, at most about 0.5 micron, at most about 0.25 micron). The thicknesses of the layers are dependent on, e.g., the thickness of the device being formed, the number of layers, the materials of the layers, and/or the configurations of the layers. The total thickness of balloon 22 can be relatively constant, but in some cases, the total thickness of the balloon can vary along its length.

Along a radial cross section of a balloon, the thickness of the flexible and stiff layers may be different or the same. In some relatively stiff portions, the flexible layers make up from about one percent to about 45% (e.g., from about 5% to about 45%, from about 5% to about 40%), about 30% or less, from about 20% to about 30%) of the total balloon wall thickness and stiff polymer makes up the balance. In certain relatively flexible portions, the stiff layers make up from about one percent to about 45% (e.g., from about 5% to about 45%, from about 5% to about 40%, about 30% or less, from about 20% to about 30%) of the total balloon wall thickness and flexible polymer makes up the balance. For a device with a comparable number of flexible and stiff layers, the flexible polymer layers may be thinner or thicker than the stiff polymer layers. The thickness of the layers may vary progressively in a radial direction. For example, the layers may get thicker from the outermost layer to the innermost layer or vice versa. The thickness of the layers of one type (flexible or stiff) may vary while the layers of the other type are constant.

The change in thickness in one or more layers can occur abruptly (e.g., step-wise) or gradually (e.g., over about 0.25 inch or more). The change in thickness can occur anywhere along the length of the balloon, e.g., at the interface between the cone portions and the body portion, along the sleeves, or at a predetermined position in the body portion.

The number of layers is generally two or more. For example, the number of layers can be at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, or more. In certain embodiments, the number of layers is less than 100 (e.g., less than 90, less than 80, less than 70, less than 60, less than 50, less than 40, less than 35, less than 30, less than 25, less than 20, less than 15, or less than 10). The number of layers may be, for example, seven, thirteen, twenty or more.

In some embodiments, increasing the number of layers can increase the puncture resistance of a balloon or tube. For example, the puncture resistance of a balloon having four layers can be higher than a balloon having the same material make up (i.e., the same percentage of each chemical component, such a polymer and/or an additive) and the same double thickness but formed of two layers. In certain embodiments, a balloon having more than three layers (e.g., four layers, five layers, six layers, seven layers, eight layers, nine layers, 10 layers, 11 layers, 12 layers, 13 layers, 20 layers, etc.) can have a puncture resistance that is at least about three percent higher (e.g., at least about five percent, at least about 10 percent, at least about 20 percent, at least about 30 percent) higher than a balloon having less than three layers (e.g., one layer, two layers or three layers) that has the same material make up and the same double wall thickness as the balloon having more than three layers.

Figure 8:
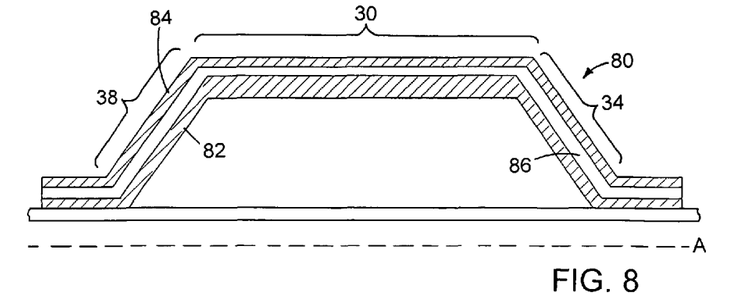
FIG. 8 is a cross-sectional illustration of an embodiment of a balloon.

As an example, referring to FIG. 8, a balloon wall 80 includes three layers of alternating two hard layers 82 and 84, and a soft layer 86 between hard layers 82 and 84. Hard layer 82 increases in thickness from cone portions 34 and 38 to body portion 30. Hard layer 84 has substantially constant thickness along substantially the entire length of the balloon. Soft layer 86 decreases in thickness from cone portions 34 and 38 to body portion 30. As a result, cone portions 34 and 38 are relatively flexible compared to body portion 30. Balloons with more than two layers can have any of the combination of configurations described here. For example, one or more of layers 82, 84, and 86 can be tapered (e.g., FIG. 2).

A balloon can have any combination of the layers described above, formed of two or more materials. For example, a balloon can have one or more layers of constant or varying thickness, arranged evenly apart or asymmetrically, etc.

Materials

Any of the materials described below can be used for any of the layers described herein, in any combination. Hardness or softness is typically considered relative to other polymers in the balloon. Two or more materials can be used in a given layer.

In some embodiments, the layers may include stiff or hard polymer that has a hardness of more than about 60 Shore D, e.g., 65 Shore D or more, and/or softer polymer that has a hardness of about 60 Shore D or less. In some embodiments, the flexible or soft polymer can have a hardness of greater than about 60 Shore D, but it is still softer than the hard polymer. The difference in hardnesses of adjacent bonded layers can be about 40 Shore D or less, preferably 20 Shore D or less, which can enhance compatibility between the layers, reduce delamination at the interface, and/or increase ease of coextruding. Hardness may be measured according to ASTM D2240. The layers can alternate between hard and soft polymer. The layers may be of progressively increasing hardness. For example, the layers may be of progressively increasing hardness from the innermost layer to the outermost layer. For example, for a medical balloon used for stent delivery, the outermost layer can be a soft layer that absorbs and distributes stress and abrasion imposed by the stent.

The layers may be of substantially pure polymer or they may be blends of different polymers. All of the soft (or hard) layers may be made of the same soft (or hard) polymer or the different soft (or hard) layers may be made of different polymers. The soft and hard layers can be made of block copolymers including common block moieties, which can enhance compatibility, while maintaining defect retardation. For example, the block moieties may be amide segments and tetramethylene glycol segments.

An example is the PEBAX® family of polymers, which can be used pure or as blends (available from Atofina, Philadelphia, Pa.). For example, PEBAX® 5533 (55 Shore D) can be blended with PEBAX® 2533 (25 Shore D) in a weight ratio of about 4 to 1 to provide a soft polymer of about 50 Shore D. Another combination of hard and soft polymers is polybutylene terephthalate (PBT) such as CELANEX® (over 80 Shore D, from Ticona, Summit, N.J.) and polyester/ether block copolymer available as ARNITEL® (55 Shore D, from DSM, Erionspilla, Ind.). A combination of hard and soft polymers is PBT and one or more PBT thermoplastic elastomers, such as RITEFLEX® (55 Shore D from Ticona in Summit, N.J.) and HYTREL® (55 Shore D from E. I. Dupont de Nemours, Wilmington, Del.) for example. Still another combination of hard and soft polymers is polyethylene terephthalate (PET) and a thermoplastic elastomer, such as a PBT thermoplastic elastomer (e.g., ARNITEL®, HYTREL®, or RITEFLEX®).

In certain embodiments, one or more layers can contain one or more nylons. For example, one or more of the hard polymer layers can contain one or more nylons. For example, a combination of hard and soft polymers is a nylon and a PEBAX®-type material, such as PEBAX®, GRILON®, GRILAMID® (EMS) and/or VESTAMID® (Creanova). Examples of nylons include aliphatic nylons, such as Nylon 11 (Elf Atochem), Nylon 6 (Allied Signal), Nylon 6/10 (BASF), Nylon 6/12 (Ashley Polymers) and Nylon 12. Additional examples of nylons include aromatic nylons, such as GRIVORY® (EMS) and Nylon MXD-6. Other nylons and/or combinations of nylons can be used.

In some embodiments, one or more layers can contain a liquid crystal polymer (LCP) (e.g., a composite material having the LCP incorporated therein). Examples of LCPs include polyester(s), polyamide(s) and/or their copolymers, such as VECTRA® A (Ticona), VECTRA® B (Ticona) and VECTRA® LKX (Ticona) (e.g., VECTRA® LKX 1111 (Ticona)). Other LCPs and/or combinations of LCPs can be used.

The LCP can be incorporated into one or more polymers, such as, for example, a PEBAX®-type material, a nylon, a thermoplastic polyester and/or thermoplastic elastomer versions thereof. In certain embodiments, the liquid crystal polymer can be incorporated into one or more of the polymer layers to form a hard layer of material (e.g., a layer of material with more than about 60 Shore D hardness, such as more than about 65 Shore D hardness). In another combination, an LCP is incorporated into a layer containing one or more PEBAX®-type materials, such as PEBAX®, GRILON®, GRILAMID®, and/or VESTAMID®. In certain embodiments, an LCP-containing composition can be relatively stiff in the direction of melt flow. Without wishing to be bound by theory, it is believed that this may result because LCP crystals (e.g., fibers) form or align in the melt flow direction as the polymer composite cools from a liquid state to a solid state. In embodiments in which a tube is formed into a medical balloon (described below), it is believed that the LCP fibers can reinforce the other polymer(s) contained in the layer (e.g., matrix polymer(s)), which can restrict the balloon from growing in length during inflation while, depending on the LCP content in the composite material, permitting the balloon to be inflated.

The amount of LCP contained in the layer(s) of the balloon can vary depending upon its intended use. In some embodiments, as the percentage of LCP in a composite material is decreased, the individual layer thickness and the overall thickness of one or more layers of an LCP-containing composite material, e.g., in a balloon, can be increased. For example, within a given layer, the LCP content can be at least about 0.1 weight percent (e.g., from about one weight percent to about 50 weight percent, from about five weight percent to about 20 weight percent, from about five weight percent to about 15 weight percent).

In certain embodiments, an adhesion enhancing material can be incorporated into one or more material layers. An adhesion enhancing material can be used, for example, to enhance the adhesion between adjacent layers. Examples of adhesion enhancing materials include epoxy or anhydride modified polyolefins, such as LOTADER® (Elf Atochem) and KODAR® PETG (Eastman Kodak). An adhesion enhancing material can be added to a material (e.g., a composition containing one or more polymers) prior to extrusion (described below). For example, in embodiments in which alternate layers are formed of PET and PBT, PETG can be added to the PET before extrusion.

The amount of adhesion enhancing material can vary depending upon the intended use. In some embodiments, a sufficient amount of adhesion enhancing material(s) is included in the material so that the adhesion enhancing material(s) makes up at least about 0.5 percent of the resulting mixture that forms the layer (e.g., at least about one percent, at least about five percent, at least about 10 percent) and/or at most about 20 percent of the resulting mixture that forms the layer (e.g., at most about 15 percent, at most about 12 percent, at most about 10 percent).

In some embodiments, a compatibilizing material can be incorporated into one or more material layers. The compatibilizing material can be designed, for example, to modify one or more phase boundaries of the LCP(s) and one or more of the other polymer(s) (e.g., thermoplastic polymer(s)) and/or to enhance adhesion between the LCPs and one or more of the other polymer(s). The compatibilizing material can be a copolymer, such as a block copolymer, including moieties of at least two different chemical structures, respectively providing compatibility with an LCP and one or more other polymers in the mixture. The compatibilizing material can be a reactive polymer that reacts with the LCP and/or one or more other polymers in the mixture. The compatibilizing material can be a catalyst that promotes a reaction between the LCP and one or more other polymers in the mixture. Other compatibilizing materials can be used. Combinations of compatibilizing materials can be used.

Examples of compatibilizing materials include copolyester elastomers, ethylene unsaturated ester copolymers, such as ethylene-maleic anhydride copolymers, copolymers of ethylene and a carboxylic acid or acid derivative, such as ethylene-methyl acrylate copolymers, polyolefins or ethylene-unsaturated ester copolymers grafted with functional monomers, such as ethylene-methyl acrylate copolymers, copolymers of ethylene and a carboxylic acid or acid derivative, such as ethylene-methyl acrylate maleic anhydride terpolymers, terpolymers of ethylene, unsaturated ester and a carboxylic acid or acid derivative, such as ethylene-methyl acrylate-methacrylic acid terpolymers, maleic acid grafted styrene-ethylene-butadiene-styrene block copolymers, and acrylic acid elastomers, such as acrylic rubbers. Similar polymers containing epoxy functional groups, for instance derived from glycidyl methylacrylate (e.g., alkyl(meth)acrylate-ethylene-glycidyl (meth)acrylate polymers) can be used. Ionomeric copolymers can be used. PETG can be used. Other examples of compatibilizing materials include HYTREL® HTR-6108, POLYBOND® 3009 (BP Chemicals), SP 2205 (Chevron), DS 1328/60 (Chevron), LOTADER® 2400, ESCOR® ATX-320, ESCOR® ATX-325, VAMAC® G1 and LOTADER® AX8660. In certain embodiments, a compatibilizing material (e.g., PETG) can be mixed with one or more polymers (e.g., an LCP-containing material) prior to extrusion.

There are many ways in which LCPs can be blended into thermoplastics. The LCP blend can be a ternary system of LCP, thermoplastic and compatibilizing materials. Generally, consideration is given to the properties of the LCP and the other polymer(s) (e.g., PET), as well as the desired properties of the resulting blend, when selecting the compatibilizing material(s). Systems with multiple combinations of different LCPs, different thermoplastics and different compatibilizing materials are contemplated.

For example, the compatibilized blend can be a blend of polyazomethine LCP, a thermoplastic polymer such as a polyamide, and a compatibilizing material such as a caprolactum having at least one functional group capable of showing compatibility and/or reactivity to the LCP and/or the thermoplastic polymer. Such blends are described, for example, in U.S. Pat. No. 5,565,530, which is hereby incorporated by reference.

Other examples include a polymer blend product including PET, a wholly aromatic LCP copolyester and an ethylene-methyl acrylate-acrylic acid terpolymer compatibilizing material, such as, for example, ESCOR® ATX320, ESCOR® ATX325, or ESCOR® XV-11.04. Another polymer blend product includes PET, a wholly aromatic LCP copolyester and an ethylene-maleic anhydride copolymer compatibilizing material, such as POLYBOND® 3009. Another polymer blend product includes PET, a wholly aromatic LCP copolyester and an ethylene-methyl acrylate copolymer grated with maleic anhydride compatibilizing material, such as DS 1328/60, or a copolyester elastomer, such as HYTREL® HTR 6108.

Polymer blend products including PET, LCP and at least two compatibilizing materials can be used. For example, DS 1328/60 and POLYBOND® 3009 can be used with the LCP VECTRA®. As an additional example, when the LCP is VECTRA®, the compatibilizing materials can be POLYBOND® 3009 and at least one additional compatibilizing material selected from ESCOR® ATX-320, ESCOR® ATX-325, DS 1328160, ESCOR® XV-11.04 and HYTREL® HTR-6108.

In some embodiments containing an LCP, a thermoplastic polymer and compatibilizing material(s), the blend product includes from about 0.1 weight percent to about 10 weight percent (e.g., from about 0.5 weight percent to about 2 percent) LCP, from about 40 weight percent to about 99 weight percent (e.g., from about 85 weight percent to about 99 weight percent) thermoplastic polymer, and from about 0.1 weight percent to about 30 weight percent (e.g., from about one weight percent to about 10 weight percent) compatibilizing material(s).

While certain polymers and polymer combinations are discussed above, other polymers and polymer combinations can also be used. Other polymers include, for example, elastomers such as thermoplastic elastomers and engineering thermoplastic elastomers, such as polybutylene terephthalate-polyethene glycol block copolymers, which are available, for example, as HYTREL®. These are discussed in Hamilton U.S. Pat. No. 5,797,877, the entire content of which is incorporated herein by reference. Other polymers include polyurethenes. Other polymers include copolymers such as ABS (acrylonitrile-butadiene-styrene), ABS/nylon, ABS/-polyvinyl chloride (PVC), ABS/polycarbonate, acrylonitrile copolymer, polyacrylamide, polyacrylate and polyacrylsulfone, polyesters such as polyethylene terephthalate (PET), polybutylene terephthalate (PBT), polyethylene naphthalate (PEN), liquid crystal polymer (LCP), polyester/polycaprolactone and polyester/polyadipate; and high melt temperature polyethers including polyetheretherketone (PEEK), polyethersulfone (PES), polyetherimide (PEI) and polyetherketone (PEK), polymenthylpentene, polyphenylene ether, polyphenylene sulfide, and styrene acrylonitrile (SAN), polyamides such as nylon 6, nylon 6/6, nylon 6/66, nylon 6/9, nylon 6/10, nylon 6/12, nylon 11, nylon 12, ethylene, propylene ethylene vinylacetate and ethylene vinyl alcohol (EVA), various ionomers, polyethylene type I-IV, polyolefins, polyurethane, polyvinyl chloride, and polysiloxanes (silicones). Those with low to medium melt temperatures include fluorocarbons such as polychlorotriethylene (CTFE), poly[ethylene-co-chlorotrifluoroethylene] (ECTFE) copolymer ethylene tetrafluoroethylene (ETFE), copolymer tetrafluoroethylene and hexafluoropropylene (FEP), perfluoroalkane (PFA) and poly[vinylidene fluoride] (PVDF).

In other embodiments, one or more adhesive layers can be formed between layers of other materials. The adhesive layer(s) can be used, e.g., to enhance the adhesion between two or more layers, such as when the two or more layers are immiscible.

As an example, one or more layers can be formed of any polyester-containing material (e.g., a substantially pure polyester, a blend containing at least one polyester) appropriate for use in a medical device. Such polymers include, for example, polyester homopolymers and/or copolymers (e.g., block copolymers) of polyesters. Examples of polyesters include PET polymers, PBT polymers and blends and combinations thereof, such as the SELAR® PT family of polymers (e.g., SELAR® PT 8307, SELAR® PT4274, SELAR® PTX280, DuPont (Wilmington, Del.)), the CLEARTUF® family of polymers (e.g., CLEARTUF® 8006, M&G Polymers (Apple Grove, W. Va.)), the TRAYTUF® family of polymers (e.g., TRAYTUF® 1006, Shell Chemical (Houston, Tex.), the MELINAR® family of polymers, DuPont, the CELANEX® family of polymers, Ticona (Summit, N.J.), the RITEFLEX® family of polymers, Ticona, the HYTREL® family of polymers (e.g., HYTREL® 5556, HYTREL®

7246, HYTREL® 4056), DuPont, and the ARNITEL® family of polymers (e.g., ARNITEL® EM630), DSM (Erionspilla, Ind.).

The other layer(s) can be formed of any polyamide-containing material (e.g., a substantially pure polyamide, a blend containing at least one polyamide) appropriate for use in a medical device. Such polymers include, for example, polyamide homopolymers and/or copolymers (e.g., block copolymers) of polyamides. One type of polyamide includes the nylon family of polymers, including, for example, aliphatic nylons and aromatic nylons, such as, e.g., Nylon 11 (Atofina (Philadelphia, Pa.)), Nylon 6 (Honeywell (Morristown, N.J.)), Nylon 6/10 (BASF (Mount Olive, N.J.)), Nylon 6/12 (Ashley Polymers (Cranford, N.J.)), Nylon 12, Nylon MXD-6, the GRIVORY® family of polymers (EMS (Sumter, S.C.)), the GRILAMID® family of polymers (EMS), the VESTAMID® family of polymers (Daicel-Degussa Ltd), and the PEBAX® family of polymers (e.g., PEBAX® 5533, PEBAX® 2533, PEBAX® 7033, Atofina).

The adhesive layer(s) can be formed any adhesive material appropriate for use in a medical device. The adhesive material can be a polymer (e.g., a substantially pure polymer, or a blend of polymers). As an example, in certain embodiments, the adhesive material is formed of an ethylene vinyl acetate polymer-containing material. As another example, in some embodiments, the adhesive material is formed of an anhydride-modified polyolefin. An adhesive can be selected, for example, from the BYNEL® family of polymers (e.g., BYNEL® CXA Series, BYNEL® 1000 Series, BYNEL® 1123, BYNEL® 1124, BYNEL® 11E554, BYNEL® 11E573, BYNEL® CXA E-418), commercially available from E. I. DuPont de Nemours (Wilmington, Del.), the PLEXAR® family of polymers (e.g., PX360, PX360E, PX380, PX3227, PX3236, PX3277, PX5125, PX5327, PX206, PX209, PX2049, PX165, PX175, PX180, PX909, PX101, PX107A, PX108, PX114, PX1164), commercially available from Equistar Chemicals (Newark, N.J.), and/or the BLOX® family of polymers (e.g., BLOX® 200 Series), commercially available from the Dow Chemical Company (Midland, Mich.).

Manufacture

Balloon 22 can be made by forming a tube and forming the tube into the balloon.

For example, a tube can be prepared by an extrusion process. Generally, this process can involve the use of an extrusion apparatus (e.g., a crosshead, such as a compact crosshead) having a series of discs. A suitable extrusion apparatus, including some illustrative operating conditions, such as zone heating temperatures, polymer concentrations, feed rate, and line speed, are described in U.S. Ser. No. 09/798,749, entitled "Multilayer Medical Device" and filed on Mar. 2, 2001, and the attached Appendix, all hereby incorporated by reference in its entirety.

An exemplary system for controlling the feed rate or flow of polymers, including melt pumps, and systems and methods for controlling the pumps, is also described in WO 01/32398, entitled "Method and Apparatus for Extruding Catheter Tubing", hereby incorporated by reference in its entirety. Other methods include using servo-controlled valves, as described in Burlis et al., U.S. Pat. No. 3,752,617, hereby incorporated by reference.

Next, to form a balloon, the formed (e.g., co-extruded) tube can be blow molded. In some embodiments, the tube is placed (e.g., centered) in a preheated balloon mold, and air is introduced into the tube to maintain the patency of the tube lumen. After soaking at a predetermined temperature and time, the tube is stretched for a predetermined distance at a predetermined time, rate, and temperature. The pressure inside the tube is then sufficiently increased to radially expand the tube inside the mold to form the balloon. The formed balloon can be heat treated, for example, to enhance folding memory, and/or folded into a predetermined profile.

In some cases, molding of the balloon can form relatively thick-walled cone portions, which can reduce the flexibility and trackability of the balloon. For example, during molding, the body portion of the balloon can be stretched diametrically by at least a factor of six. As a result, the balloon wall in the body portion can be relatively thin because of the relatively large amount of stretching. However, portions of the balloon other than the body portion may stretch relatively little. For example, the ends of the balloon may remain approximately the same diameter as the catheter shaft and may be stretched by approximately a factor of two. As a result, the portions of the balloon other than the body portion can remain relatively thick and be inflexible. By forming the balloons as described herein, the flexibility of the portions of the balloon (e.g., other than the body portion) can be enhanced.

Methods of forming a balloon from a tube are described in, for example, Bertolino U.S. Pat. No. 6,946,092; Anderson U.S. Pat. No. 6,120,364; Wang U.S. Pat. No. 5,714,110; and Noddin U.S. Pat. No. 4,963,313, all hereby incorporated by reference in their entirety. Other suitable balloon catheter systems are described in, for example, Wang U.S. Pat. No. 5,195,969; Hamlin U.S. Pat. No. 5,270,086; and exemplified by the RANGER® system available from Boston Scientific Scimed, Maple Grove, Minn. The catheter shaft may also be any of the multilayer tubes described in the attached Appendix, Ser. No. 10/645,014.

Numerous other embodiments are contemplated. For example, any of the embodiments, e.g., configurations, of tubes described in the attached Appendix can be used to form a medical balloon. Having a multitude of thin layers can distribute stresses and defects, such as cracks or punctures, so that they are less likely to propagate through the wall of the balloon to the point of causing a failure. Different layers formed of different hardness can assist in distributing stress and retard defect propagation, while providing high burst strength and low distention. The layers can be formed to be thicker than the typical size of defects, e.g., gas bubbles formed in the extrusion or foreign particles.

All of the features disclosed herein may be combined in any combination. Each feature disclosed may be replaced by an alternative feature serving the same, equivalent, or similar purpose. Thus, unless expressly stated otherwise, each feature disclosed is only an example of a generic series of equivalent or similar features.

All publications, applications, patents, and references referred to in this application are herein incorporated by reference in their entirety.

Other embodiments are within the claims.

What is claimed is:
1. A medical balloon, comprising:
an expandable balloon including an inner layer and an outer layer;
wherein the balloon includes a proximal waist, a proximal cone, a body portion, a distal cone and a distal waist;
wherein the inner layer has a greater thickness in the body portion than in the proximal waist; and
wherein the outer layer has a lesser thickness in the body portion than in the proximal waist.
2. The medical balloon of claim 1, wherein a sum of the thicknesses of the inner and outer layers is substantially constant over the length of the balloon.

3. The medical balloon of claim 1, wherein in the body portion, the inner layer has a greater thickness than the outer layer.

4. The medical balloon of claim 1, wherein in the proximal and distal waists, the outer layer has a greater thickness than the inner layer.

5. The medical balloon of claim 1, wherein the inner and outer layers are formed from different polymer compositions.

6. The medical balloon of claim 5, wherein the outer layer is less stiff, more flexible, more compliant, and is formed from a lower durometer polymer than the inner layer.

7. The medical balloon of claim 6, wherein the outer layer is formed from a more amorphous polymer than the inner layer.

8. The medical balloon of claim 1, wherein the body portion has higher strength and lower elasticity than the proximal and distal waists and the proximal and distal cones.

9. The medical balloon of claim 1, wherein the outer layer is disposed substantially entirely on the inner layer.

10. A balloon catheter, comprising:
a catheter shaft having a longitudinal axis;
an expandable balloon including inner and outer layers that extend substantially along a length of the balloon;
wherein the length of the balloon includes a proximal waist, a proximal cone distal to the proximal waist, a body portion distal to the proximal waist, a distal cone distal to the body portion, and a distal waist distal to the distal cone;
wherein the proximal and distal waists are attached to the catheter shaft;
wherein during expansion of the balloon, the body portion expands radially, the proximal and distal waists do not expand radially, and the proximal and distal cones extend from the body portion to the proximal and distal waists, respectively;
wherein the inner layer has a greater thickness in the body portion than in the distal waist; and
wherein the outer layer has a lesser thickness in the body portion than in the distal waist.

11. The balloon catheter of claim 10, wherein a sum of the thicknesses of the inner and outer layers is substantially constant over the length of the balloon.

12. The balloon catheter of claim 10, wherein in the body portion, the inner layer has a greater thickness than the outer layer.

13. The balloon catheter of claim 10, wherein in the proximal and distal waists, the outer layer has a greater thickness than the inner layer.

14. The balloon catheter of claim 10, wherein the outer layer is less stiff, more flexible, more compliant, is formed from a lower durometer polymer than the inner layer, and is formed from a more amorphous polymer than the inner layer.

15. The balloon catheter of claim 10, wherein the body portion has higher strength and lower elasticity than the proximal and distal waists and the proximal and distal cones.

16. A medical balloon, comprising:
an expandable balloon including inner and outer layers that extend substantially along a length of the balloon;
wherein the length of the balloon includes a proximal waist, a proximal cone distal to the proximal waist, a body portion distal to the proximal waist, a distal cone distal to the body portion, and a distal waist distal to the distal cone;
wherein during expansion of the balloon, the body portion expands radially, the proximal and distal waists do not expand radially, and the proximal and distal cones extend from the body portion to the proximal and distal waists, respectively;
wherein the inner layer has a greater thickness in the body portion than in the proximal waist;
wherein the outer layer has a lesser thickness in the body portion than in the proximal waist;
wherein a sum of the thicknesses of the inner and outer layers is constant over the length of the balloon;
wherein in the body portion, the inner layer has a greater thickness than the outer layer; and
wherein in the proximal waist, the outer layer has a greater thickness than the inner layer.

* * * * *